United States Patent
Brewer et al.

(10) Patent No.: US 9,549,690 B2
(45) Date of Patent: Jan. 24, 2017

(54) SYSTEM AND METHOD FOR DETERMINING DEAD SPACE FRACTION IN AN ONGOING MANNER FROM INTERMITTENT BLOOD GAS SAMPLES

(75) Inventors: Lara Brewer, Bountiful, UT (US); Joseph Allen Orr, Park City, UT (US)

(73) Assignee: Koninklijke Philips N.V., Eindhoven (NL)

(*) Notice: Subject to any disclaimer, the term of this patent is extended or adjusted under 35 U.S.C. 154(b) by 973 days.

(21) Appl. No.: 13/518,955

(22) PCT Filed: Dec. 27, 2010

(86) PCT No.: PCT/IB2010/056086
§ 371 (c)(1),
(2), (4) Date: Jun. 25, 2012

(87) PCT Pub. No.: WO2011/080695
PCT Pub. Date: Jul. 7, 2011

(65) Prior Publication Data
US 2012/0289853 A1    Nov. 15, 2012

Related U.S. Application Data

(60) Provisional application No. 61/290,648, filed on Dec. 29, 2009.

(51) Int. Cl.
*A61B 5/08* (2006.01)
*G06F 19/00* (2011.01)

(52) U.S. Cl.
CPC ............. *A61B 5/08* (2013.01); *A61B 5/082* (2013.01); *G06F 19/3406* (2013.01)

(58) Field of Classification Search
CPC ............. A61B 5/08; A61B 5/091; A61B 5/93; A61B 5/0935; G06F 19/3406
USPC ................................................. 600/529–543
See application file for complete search history.

(56) References Cited

U.S. PATENT DOCUMENTS

| 5,402,796 A * | 4/1995 | Packer ................. A61B 5/0836 128/200.24 |
| 6,099,481 A * | 8/2000 | Daniels et al. ................ 600/538 |
| 6,217,524 B1 * | 4/2001 | Orr et al. ....................... 600/504 |
| 2003/0045807 A1 | 3/2003 | Daniels |

(Continued)

FOREIGN PATENT DOCUMENTS

| JP | 1994502090 A | 3/1994 |
| JP | 2008212686 A | 9/2008 |
| WO | 2008039412 A2 | 4/2008 |

OTHER PUBLICATIONS

Kline et al. "Diagnostic accuracy of a bedside D-dimer assay and alveolar dead-space measurement for rapid exclusion of pulmonary embolism: a multicenter study," JAMA, 285 (2001), pp. 761-768.*

(Continued)

*Primary Examiner* — Navin Natnithithadha
*Assistant Examiner* — Eric Messersmith

(57) ABSTRACT

A system is configured to monitor the dead space fraction of a subject in a substantially ongoing manner, rather than only updating the dead space fraction of the subject if one or more blood gas parameters of the subject are measured. This may facilitate enhanced control over respiratory therapy being provided to the subject, may inform decisions about care of the subject, and/or may provide other enhancements.

15 Claims, 1 Drawing Sheet

(56) References Cited

U.S. PATENT DOCUMENTS

2007/0000494 A1    1/2007   Banner et al.

OTHER PUBLICATIONS

Sinha et al., "Ventilatory ratio: a simple bedside measure of ventilation." Br J Anaesth. May 2009;102(5):692-7. doi: 10.1093/bja/aep054. Epub Apr. 3, 2009.*

Hardman et al., "Estimation of alveolar deadspace fraction using arterial and end-tidal CO2: a factor analysis using a physiological simulation." Anaesth Intensive Care. Oct. 1999;27(5):452-8.*

Fletcher et al., "Deadspace and the single breath test for carbon dioxide during anaesthesia and artificial ventilation. Effects of tidal volume and frequency of respiration." Br J Anaesth. Feb. 1984;56(2):109-19.*

\* cited by examiner

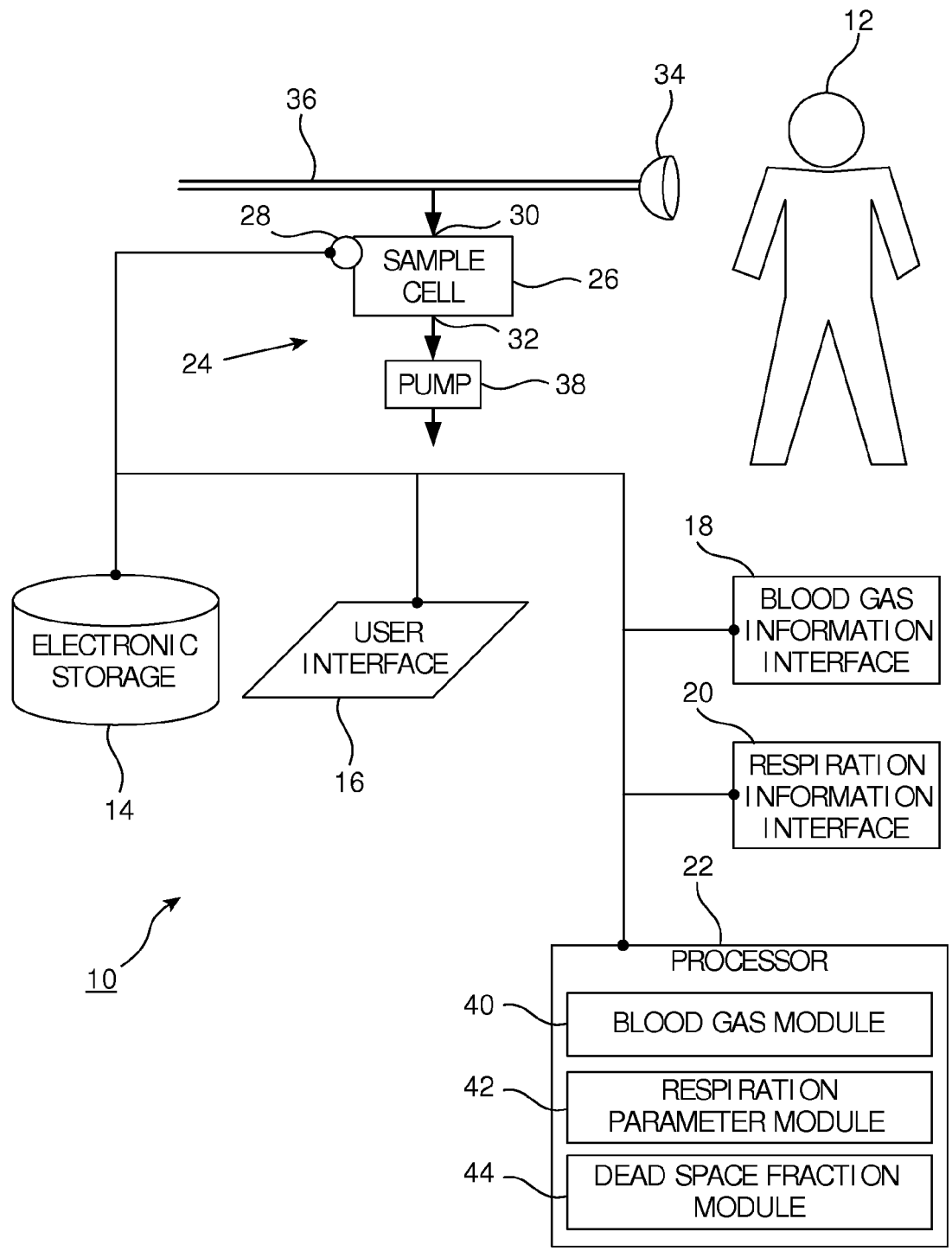

SYSTEM AND METHOD FOR DETERMINING DEAD SPACE FRACTION IN AN ONGOING MANNER FROM INTERMITTENT BLOOD GAS SAMPLES

BACKGROUND OF THE INVENTION

1. Field of the Invention

The invention relates to determining dead space fraction of a subject based on blood gas measurements that are taken only intermittently.

2. Description of the Related Art

Systems configured to determine dead space fraction are known. Generally, dead space fraction refers to the ration between respiratory dead space and tidal volume. Respiratory dead space refers to the volume of each breath by a subject that does not participate in gas exchange with the blood of the subject. For example, this volume would include the airway of the subject outside of the lungs and any volume in the lungs of the subject which is ventilated but not perfused and therefore does not participate in gas exchange. The dead space fraction of a subject can be used for diagnosis, to tailor therapy to the subject's needs, and/or for other purposes In order to determine dead space fraction in conventional systems, a blood gas measurement must be taken. This generally requires blood to be collected from a subject for each determination of dead space fraction. As such, dead space fraction is typically only updated intermittently (e.g., at intervals of about 24 hours while the patient is in intensive care).

SUMMARY OF THE INVENTION

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 1 illustrates a system configured to monitor the dead space fraction of a subject, in accordance with one or more embodiments of the invention.

DETAILED DESCRIPTION OF THE EXEMPLARY EMBODIMENTS

FIG. 1 illustrates a system 10 configured to monitor the dead space fraction of a subject 12. In particular, system 10 is configured to monitor the dead space fraction of subject 12 in a substantially ongoing manner, rather than only updating the dead space fraction of subject 12 if one or more blood gas parameters of subject 12 are measured. This may facilitate enhanced control over respiratory therapy being provided to subject 12, may inform decisions about care of subject 12, and/or may provide other enhancements. In one embodiment, system 10 includes electronic storage 14, a user interface 16, a blood gas information interface 18, a respiration information interface 20, a processor 22, and/or other components.

In one embodiment, electronic storage 14 comprises electronic storage media that electronically stores information. The electronic storage media of electronic storage 14 may include one or both of system storage that is provided integrally (La, substantially non-removable) with system 10 and/or removable storage that is removably connectable to system 10 via, for example, a port (e.g., a USB port, a firewire port, etc.) or a drive (e.g., a disk drive, etc.). Electronic storage 14 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 14 may store software algorithms, information determined by processor 22, information received via user interface 16, and/or other information that enables system 10 to function properly. Electronic storage 14 may be a separate component within system 10, or electronic storage 14 may be provided integrally with one or more other components of system 10 (e.g., processor 22).

User interface 16 is configured to provide an interface between system 10 and a user (e.g., the user, a caregiver, a therapy decision-maker, etc.) through which the user may provide information to and receive information from system 10. This enables data, results, and/or instructions and any other communicable items, collectively referred to as "information," to be communicated between the user and system 10. Examples of interface devices suitable for inclusion in user interface 16 include a keypad, buttons, switches, a keyboard, knobs, levers, a display screen, a touch screen, speakers, a microphone, an indicator light, an audible alarm, and a printer.

It is to be understood that other communication techniques, either hard-wired or wireless, are also contemplated by the present invention as user interface 16. For example, the present invention contemplates that user interface 16 may be integrated with a removable storage interface provided by electronic storage 14. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 16 include, but are not limited to, an RS-232 port, RF link, an IR link, modem (telephone, cable or other). In short, any technique for communicating information with system 10 is contemplated by the present invention as user interface 16.

The blood gas information interface 18 is configured to receive blood gas information to system 10. Blood gas information includes information related to one or more blood gas parameters. The blood gas parameters indicate concentrations (e.g., partial pressure) of one or more molecular species in the blood of subject 12. By way of non-limiting example, the one or more molecular species may include one or more of oxygen, carbon dioxide, bicarbonate, and/or other molecular species. In one embodiment, blood gas information interface 18 includes an electronic port, lead, wireless receiver, and/or other component enabling electronic reception of blood gas information to system 10. The blood gas information may be received electronically from a detector configured to measure the one or more blood gas parameters. In one embodiment, blood gas information interface 18 includes a user interface (e.g., user interface 16) through which the user can manually input the blood gas information. In one embodiment, blood gas information is entered manually from a printout, a patient chart, a log book, and/or some other reference.

The respiration information interface 20 is configured to receive respiration information. Respiration information includes information related to one or more respiration parameters of the breathing of subject 12. The one or more respiration parameters may include one or more of pressure, flow rate, tidal volume, alveolar tidal volume, composition (e.g., partial pressure(s), concentration(s), etc.), expired carbon dioxide, respiratory rate, volume of expired carbon dioxide, missed expired carbon dioxide fraction, airway dead volume, apparatus dead volume, and/or other respiration parameters. In one embodiment, respiration information interface 20 includes an electronic port, lead, wireless receiver, and/or other component enabling electronic reception of respiration information from a respiration detector 24.

Respiration detector 24 is configured to obtain gas from at or near the airway of subject 12, and to generate output signals conveying information obtained from measurements taken from the obtained gas. In one embodiment, respiration detector 24 includes a sampling chamber 26 and a sensor 28.

The sampling chamber 26 is configured to receive gas obtained at or near the airway of subject 12. The gas flows through sampling chamber 26 from an inlet 30 to an outlet 32. The gas is conveyed to sampling chamber 26 via a subject interface appliance 34 and/or a conduit 36. The subject interface appliance 34 may engage one or more orifices of the airway of subject 12 in a sealed or unsealed manner. Some examples of subject interface appliance 34 may include, for example, an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present invention is not limited to these examples, and contemplates implementation of any subject interface. The sampling chamber may be placed directly in conduit 36. In this configuration, a pump may not be needed.

The conduit 36 is configured to place inlet 30 of sampling chamber 26 in fluid communication with subject interface appliance 34 such that gas obtained by subject interface appliance 34 from at or near the airway of subject 12 is provided to inlet 30 via conduit 36. In one embodiment, respiration detector 24 is configured for sidestream sampling. In this configuration, conduit 36 is further configured to place subject interface appliance 34 in fluid communication with a source of a breathable substance. For example, a flow of breathable gas may be delivered to subject 12 through conduit 36 having one or more parameters that are controlled in accordance with a therapy regime. The one or more parameters of the flow of breathable gas that are controlled may include one or more of pressure, flow rate, composition, humidity, temperature, and/or other parameters. In one embodiment, respiration detector 24 is configured for mainstream sampling. In this configuration, sampling chamber 26 is disposed within the flow path through sampling chamber 26, rather than being disposed off to the side (as is shown in FIG. 1). In one embodiment in which respiration detector 24 is configured for sidestream sampling, or in which conduit 36 does not provide for provision of a breathable substance to the airway of subject 12, a pump 38 is configured to draw gas from conduit 36 into sampling chamber 26 through inlet 30.

The sensor 28 is configured to generate output signals conveying information related to one or more parameters of the gas within sampling chamber 26. By way of non-limiting example, the one or more parameters of the gas may include composition, pressure, flow rate, and/or other parameters. In one embodiment, since the gas within sampling chamber 26 has been obtained from at or near the airway of subject 12, the output signals generated by sensor 28 become the respiration information communicated to system 10 through respiration information interface 20. In one embodiment, sampling chamber 26 includes one or more components that process (at least preliminarily) the output signals of sensor 28 before communicating the respiration information to system 10 through respiration information interface 20.

It will be appreciated that the illustration of sensor 28 in FIG. 1 as a single component is not intended to be limiting. In one embodiment, sensor 28 includes a plurality of sensors. Further, the location of sensor 28 within sampling chamber 26 is not intended to be limiting. The sensor 28 may include one or more sensing units disposed in conduit 36, subject interface appliance 34, at the source of the breathable substance, at or near pump 38, and/or disposed at other locations outside of sampling chamber 26. For example, sensor 28 may include a sensor disposed in conduit 36 to measure airway dead volume, tidal volume, volume of expired carbon dioxide, and/or other parameters.

Processor 22 is configured to provide information processing capabilities in system 10. As such, processor 22 may include one or more of a digital processor, an analog processor, a digital circuit designed to process information, an analog circuit designed to process information, a state machine, and/or other mechanisms for electronically processing information. Although processor 22 is shown in FIG. 1 as a single entity, this is for illustrative purposes only. In some implementations, processor 16 may include a plurality of processing units. These processing units may be physically located within the same device, or processor 22 may represent processing functionality of a plurality of devices operating in coordination.

As is shown in FIG. 1, processor 22 is configured to execute one or more computer program modules. The one or more computer program modules may include one or more of a blood gas module 40, a respiration parameter module 42, a dead space module 44. Processor 22 may be configured to execute modules 40, 42, and/or 44 by software; hardware; firmware; some combination of software, hardware, and/or firmware; and/or other mechanisms for configuring processing capabilities on processor 22.

It should be appreciated that although modules 40, 42, and 44 are illustrated in FIG. 1 as being co-located within a single processing unit, in implementations in which processor 38 includes multiple processing units, one or more of modules 40, 42, and 44 may be located remotely from the other modules. The description of the functionality provided by the different modules 40, 42, and 44 described below is for illustrative purposes, and is not intended to be limiting, as any of modules 40, 42, and 44 may provide more or less functionality than is described. For example, one or more of modules 40, 42, and 44 may be eliminated, and some or all of its functionality may be provided by other ones of modules 40, 42, and 44. As another example, processor 22 may be configured to execute one or more additional modules that may perform some or all of the functionality attributed below to one of modules 40, 42, and 44.

The blood gas module 40 is configured to obtain values for one or more blood gas parameters from the blood gas information received into system 10 via blood gas information interface 18. In one embodiment, the blood gas information may include values input to system 10 by a user (e.g., through user interface 16). In this embodiment, blood gas module 40 obtains the values by accessing the values input by the user. In one embodiment, the blood gas information received into system 10 via blood gas information interface 18 must be processed to obtain the values of the one or more blood gas parameters. In this embodiment, blood gas module 40 processes the blood gas information to obtain the values of the one or more blood gas parameters. The blood gas parameters may include one or more of partial pressure of arterial oxygen, partial pressure of arterial carbon dioxide, oxygen saturation, hemoglobin concentration, and/or other parameters.

The respiration parameter module 42 is configured to obtain values for one or more respiration parameters from respiration information received by system 10 at respiration information interface 20. In one embodiment, the output signals of sensor 28, which are received at respiration information interface 20, are processed to obtain the values for the one or more respiration parameters. The one or more respiration parameters obtained by respiration parameter module 42 may include one or more of pressure, flow rate, tidal volume, alveolar tidal volume, respiratory rate, composition (e.g., partial pressure(s), concentration(s), etc.), end-tidal carbon dioxide, volume of expired carbon dioxide, mixed expired carbon dioxide fraction, airway dead volume, apparatus dead volume, and/or other parameters.

The dead space module 44 is configured to determine the dead space fraction of subject 12 based on values for the one or more blood gas parameters obtained by respiration parameter module 42 and the one or more respiration parameters obtained by dead space module 44. The blood gas information from which blood gas parameters are obtained is relatively infrequently. This is because getting the blood gas information involves drawing blood from subject 12 and then testing the drawn blood. The respiration information, on the other hand, only requires gas to be sampled from the airway of subject 12 (which is substantially less intrusive on subject 12) and output signals from respiration detector 24 may be generated in a substantially ongoing manner. In conventional systems, determinations of dead space fraction are generally only made when the one or more blood gas information is updated (e.g., by drawing blood from subject 12). However, dead space fraction may be relatively dynamic, and determining dead space fraction in a substantially ongoing manner may enhance various aspects of diagnosis and/or treatment of subject 12.

The dead space fraction is the ratio of respiratory dead space volume to tidal volume. There are two primary components to the dead space volume parameter. The first is airway dead space, or the volume of the airway between the external orifices of subject 12 and the alveoli within the lungs of subject 12, and the second is alveolar dead space, or the volume within the lungs at which the alveoli do not function properly in conjunction with the pulmonary blood to exchange gas in the blood. The airway dead space remains substantially unchanged. The alveolar dead space may change over time, but these changes are not especially dynamic unless lung injury status has changed drastically, or ventilation/perfusion matching has been substantially altered. In contrast, the other parameter of dead space fraction, tidal volume, may be relatively dynamic, especially if the ventilation of subject 12 is being triggered spontaneously (e.g., based on attempted inspiration and exhalation by subject 12).

In order to provide a substantially ongoing determination of the dead space fraction, dead space module 44 is configured to make multiple determinations of the dead space fraction for a single set of blood gas information. For each of the multiple determinations of dead space fraction made in between a first set of blood gas information being received and a second set of blood gas information being received, the one or more blood gas parameters obtained from the first set of blood gas information is used, while updated respiration parameters (e.g., obtained from newly received respiration information) is used for each ongoing dead space fraction determination.

In one embodiment, dead space module 44 is configured to determine the dead space fraction of subject 12 at measurement intervals. These intervals may be periodic, may be triggered by the sampling rate of the respiration information (e.g., the output signals of respiration detector 24), or otherwise predetermined. In order to provide the dead space fraction in a substantially ongoing manner, the intervals may be less than about 5 hours, less than about 2 hours, less than about 1 hour, less than about 30 minutes, less than about 10 minutes, less than about 5 minutes, or less than about 2 minutes. At the end of a given interval, if new blood gas information has not been received since the last determination of dead space fraction, then dead space module 44 determines the dead space fraction from the one or more blood gas parameters used in the previous determination of dead space fraction (e.g., at the previous interval). On the other hand, generally the measurement intervals will be the same as or longer than the intervals at which respiration information is received by respiration information interface 20. As such, the determination of dead space fraction made at the end of the given interval will be made based on respiration parameter(s) obtained since the last determination of dead space fraction. Since the blood gas parameters (which are related to alveolar dead space) tend to change at a relatively low rate with respect to the respiration parameters, this implementation of "old" blood gas parameters with "new" respiration parameters to determine dead space fraction enables ongoing determination of dead space fraction without sacrificing significant accuracy and/or precision.

In one embodiment, dead space module 44 is configured to determine dead space fraction of subject 12 according to the following relationship:

$$\frac{Vd}{Vt} = \frac{(PaCO_2 - PeCO_2)}{PaCO_2}; \quad (1)$$

where Vd/Vt represents dead space fraction, $PaCO_2$ represents the partial pressure of carbon dioxide in arterial blood, and $PeCO_2$ represents the mixed expired carbon dioxide for a given breath (e.g., may be an average, a mean, and/or some other aggregated measurement, or may be measured for a single breath). As will be appreciated, $PaCO_2$ is a blood gas parameter and $PeCO_2$ is a respiration parameter. As such, in a given determination of dead space fraction, the value used for $PaCO_2$ may be "old" (e.g., the same as for a previous determination of dead space fraction), while the value used for $PeCO_2$ is "new" (e.g., obtained since the previous determination of dead space fraction).

In one embodiment, dead space module 44 is configured to determine dead space fraction of subject 12 according to the following relationship:

$$\frac{Vd}{Vt} = \frac{Vd_{alv} + Vd_{aw}}{TV}, \quad (2)$$

where $Vd_{alv}$ represents alveolar dead space, $Vd_{aw}$ represents airway dead space, and TV represents total tidal volume. The airway dead space is essentially a constant. The tidal volume is a respiration parameter that can be obtained in an ongoing manner by respiration parameter module 42 from the output signals generated by respiration detector 24. The alveolar dead space is a parameter that is derived from a combination of blood gas information and/or parameters, and respiration information and/or parameters. In one embodiment, in order to facilitate determination of dead space fraction at a given interval for which new blood gas information has not been received, a value for alveolar dead space that was used in a previous determination of dead space fraction is updated to provide an estimate of alveolar dead space for the given interval. This updating may include using respiration information received, and/or respiration parameters obtained, during the given interval to adjust the value for alveolar dead space that was used in the previous determination of dead space fraction.

For example, the alveolar dead space can be adjusted according to the following relationship:

$$Vd_{alv} = \frac{Vd_{alv_0}}{Vt_{alv_0}} Vt_{alv}, \quad (3)$$

where $Vd_{alv}$ represents an updated or adjusted determination of alveolar dead space (to be used in equation (2) shown above for the measurement interval), $Vd_{alv_0}$ represents the value of alveolar dead space used in a previous determination of dead space fraction, $Vt_{alv_0}$ represents a value of alveolar tidal volume used in the previous determination of dead space fraction, and $Vt_{alv}$ represents the value for alveolar tidal volume determined by respiration parameter module 42 for the given interval. $Vt_{alv}$ is a respiration parameter that is determined by respiration parameter module 42 from respiration information received through respiration information interface 20. In one embodiment, the value $Vt_{alv_0}$ is a value that was determined from respiration received by system 10 concomitantly with the blood gas information used to obtain $Vd_{alv_0}$ (i.e., it was obtained from the same respiration information used to determine $Vd_{alv_0}$).

Adjustment to previously obtained values of alveolar dead space to determine dead space fraction for intervals during which new blood gas information has not been received is performed by dead space module 44. In one embodiment, determination of alveolar dead space from blood gas information and respiration information received concomitantly is performed by blood gas module 40. As such, for the purposes of this disclosure determinations of alveolar dead space (not adjustments to previous determinations) are considered determinations of a blood gas parameter.

In one embodiment, user interface 16 includes an electronic display. The processor 22 is configured to control the electronic display to convey the determinations of dead space fraction by dead space module 44 to users. This provides updated values of dead space fraction to the users in a substantially ongoing manner. This may enhance diagnosis and/or treatment of subject 12 by the users. In one embodiment, system 10 includes one or more components that provide therapy to subject 12. For example, system 10 may include a ventilator configured to facilitate respiration by subject 12. One or more of the settings of the ventilator may be adjusted automatically by processor 22 based on the ongoing determination of dead space fraction.

It will be appreciated that the particular relationships used to determine dead space fraction described above. The scope of this disclosure includes at least any other relationships that enable updated determinations of dead space fraction to be made based on new respiration information and blood gas information that has been used in one or more previous determinations of dead space fraction.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system configured to monitor the dead space fraction of a subject, the system comprising:
  a blood gas information interface configured to receive blood gas information related to one or more blood gas parameters that indicate concentrations of one or more molecular species in the blood of the subject;
  a respiration information interface configured to receive respiration information related to one or more respiration parameters of the breathing of the subject; and
  a processor configured to execute computer program modules, the computer program modules comprising:
    a blood gas module configured to obtain values for the one or more blood gas parameters from the blood gas information received via the blood gas information interface;
    a respiration parameter module configured to obtain values for the one or more respiration parameters from the respiration information received via the respiration information interface; and
    a dead space fraction module configured to determine the dead space fraction of the subject based on the values for the one or more blood gas parameters obtained by the blood gas module and based on the values for the one or more respiration parameters obtained by the respiration parameter module,
  wherein
  the dead space fraction module is configured to determine the dead space fraction of the subject at measurement intervals such that, responsive to (i) blood gas information not being received by the blood gas information interface during a measurement interval, and (ii), respiration information being received by the respiration information interface during the measurement interval, the dead space fraction module determines the dead space traction of the subject at the end of the measurement interval based on values of the one or more blood, gas parameters used in a previous determination of the dead space fraction of the subject, and based on the values of the one or more respiration parameters obtained from the respiration information received during the measurement interval.

2. The system of claim 1, wherein the measurement intervals are periodic.

3. The system of claim 1, wherein the measurement intervals are less than about 10 minutes.

4. The system of claim 1, wherein the blood gas information interface comprises a user interface that facilitates manual entry of the blood gas information.

5. The system of claim 1, further comprising a user interlace configured to convey determinations of the dead space fraction by the dead space module to a user.

6. The system of claim 1, wherein:
the dead space fraction module determines the dead space fraction according to the relationship:

$$\frac{Vd}{Vt} = \frac{Vd_{alv} + Vd_{aw}}{TV}, \quad (2)$$

where $Vd_{alv}$ is an alveolar dead space, $Vd_{aw}$ is an airway dead space, and TV is a total tidal volume of the subject.

7. The system of claim 6, wherein as value for the alveolar dead space that was used in a previous determination of the dead space fraction is updated to provide an estimate of the alveolar dead space for another determination of the dead space fraction.

8. The system of claim 7, wherein the previous determination of the dead space fraction is updated using the respiration information received, or the respiration parameters obtained, during the measurement interval to adjust a value for the alveolar dead space that was used in the previous determination of the dead space fraction.

9. The system of claim 7, wherein the estimate of the alveolar dead space for the other determination of the dead space fraction is updated according to the relationship:

$$Vd_{alv} = \frac{Vd_{alv_0}}{Vt_{alv_0}} Vt_{alv}, \quad (3)$$

where $Vd_{alv}$ is an updated determination of the alveolar dead space, $Vd_{alv0}$ is a value of the alveolar dead space used in the previous determination of the dead space fraction, $Vt_{alv0}$ is a value of an alveolar tidal volume used in the previous determination of the dead space fraction, and $Vk_{alv}$, is a value for the alveolar tidal volume determined by the respiration parameter module.

10. The system of claim 9, wherein $Vt_{alv0}$ is determined from respiration received concomitantly with the blood gas information used to obtain $Vd_{alv0}$.

11. A method of monitoring the dead space fraction of a subject, the method comprising:
receiving blood gas information related to one or more blood gas parameters that indicate concentrations of one or more molecular species in the blood of a subject;
receiving respiration information related to one or more respiration parameters of the breathing of the subject;
obtaining values for one or more blood gas parameters from the received blood gas information;
obtaining values for one or more respiration parameters from the received respiration information; and
determining, at measurement intervals, the dead space fraction of the subject based on the obtained values for the one or more blood gas parameters and based on the obtained values for the one or more respiration parameters,
wherein, responsive to (i) blood gas information not being received during a measurement interval, and (ii), respiration information being received during the measurement interval, the dead space fraction, of the subject is determined at the end of the measurement interval based on values of the one or more blood gas parameters used in a previous determination of the dead space fraction of the subject, and based on the values of the one or more respiration parameters obtained during, the measurement interval.

12. The method of claim 11, wherein the measurement intervals are periodic.

13. The method of claim 11, wherein the measurement intervals are less than about 10 minutes.

14. The method of claim 11, wherein receiving the blood gas information comprises receiving blood gas information that is manually entered a user.

15. The method of claim 11, further comprising conveying the determinations of the dead space fraction to a user.

* * * * *